(12) United States Patent
Lee et al.

(10) Patent No.: US 6,232,078 B1
(45) Date of Patent: May 15, 2001

(54) METHOD FOR DIAGNOSING PRECLINICAL DIABETES BY QUANTIFICATION OF MITOCHONDRIAL DNA IN PERIPHERAL BLOOD

(75) Inventors: Hong-Kyu Lee, Dongseong Villa 1-303, #138-1, Kugi-dong, Chongno-gu, Seoul (KR), 110-011; Kyong-Soo Park; Chan-Soo Shin, both of Seoul (KR)

(73) Assignee: Hong-Kyu Lee, Seoul (KR)

( * ) Notice: Subject to any disclaimer, the term of this patent is extended or adjusted under 35 U.S.C. 154(b) by 0 days.

(21) Appl. No.: 09/630,377

(22) Filed: Aug. 1, 2000

Related U.S. Application Data

(63) Continuation-in-part of application No. 09/027,504, filed on Feb. 20, 1998, now abandoned.

(51) Int. Cl.$^7$ .............................. C12Q 1/68; C12P 19/34
(52) U.S. Cl. ............................................... 435/6; 435/91.2
(58) Field of Search ........................................ 435/6, 91.2

(56) References Cited

PUBLICATIONS

Antonetti et al., J. Clin. Invest. vol. 95, pp 1383–1388, 1995.*

Shin, C.S., J. Kor Diabetes Assoc. vol. 18, pp 344–350, 1995.*

* cited by examiner

*Primary Examiner*—W. Gary Jones
*Assistant Examiner*—Jehanne Souaya
(74) *Attorney, Agent, or Firm*—Anderson Kill & Olick, PC

(57) ABSTRACT

A method for predicting the development of type 2 diabetes before the manifestation of its symptoms in a subject, which comprises measuring the mitochondrial DNA(mtDNA) content in peripheral blood of the subject, comparing the measured mtDNA content with that of a normal control, and predicting the increased risk of development of diabetes when the subjects mtDNA content is lower than that of the normal control.

2 Claims, 5 Drawing Sheets

METHOD FOR DIAGNOSING PRECLINICAL DIABETES BY QUANTIFICATION OF MITOCHONDRIAL DNA IN PERIPHERAL BLOOD

CROSS-REFERENCE TO RELATED APPLICATION

This application is a continuation-in-part application of U.S. Ser. No. 09/027,504 filed on Feb. 20, 1998 now abandoned.

FIELD OF THE INVENTION

The present invention relates to a method for predicting the development of type 2 diabetes before the manifestation of the symptoms in a subject by measuring the mitochondrial DNA("mtDNA") content in peripheral blood.

BACKGROUND OF THE INVENTION

Diabetes mellitus is a group of metabolic diseases characterized by hyperglycemia resulting from defects in insulin secretion, insulin action or both. The chronic hyperglycemia of diabetes is associated with long-term damage, dysfunction, and failure of various organs, especially the eyes, kidneys, nerves, heart and blood vessels.

The diagnostic criteria for diabetes mellitus recommended by American Diabetes Association are 1) symptoms of diabetes plus casual plasma glucose concentration of 200 mg/dl or higher, 2) fasting plasma glucose concentration of 126 mg/dl or higher, and 3) 2-hour plasma glucose level of 200 mg/dl or higher during the oral glucose tolerance test using a glucose load containing the equivalent of 75 g anhydrous glucose dissolved in water. When any one of the above criteria is met, it must be confirmed, on a subsequent day, by any one of the three methods given above for warranting the diagnosis of diabetes (Report of the Expert Committee on the Diagnosis and Classification of Diabetes Mellitus, *Diabetes Care, Vol.* 23, Supplement 1, S4–S19 (January 2000)).

Type 2 diabetes, i.e., non-insulin dependent diabetes, is characterized by insulin resistance and relative insulin deficiency (Olefsky, J. M. et al., *Am. J. Physiol.*, 243, E15–E30 (1982)). Insulin resistance precedes overt type 2 diabetes mellitus in most cases. Detection of insulin resistance before the development of diabetes mellitus may lead to prevention of diabetes. Moreover, insulin resistance is commonly observed in syndrome X (insulin resistance syndrome) which is a loose disease category including diabetes mellitus, hypertension, hyperlipidemia and obesity. Testing for insulin resistance and preclinical diabetes includes insulin clamp technique and modified intravenous glucose tolerance test (DeFronzo et al., *Am. J Physiol.*, 237, E214–223 (1979)). However, these testing methods are complicated and time-consuming and, moreover, the insulin clamp technique is not suitable for applying to many people simultaneously. Accordingly, there has existed a need to develop a more convenient method for preclinically diagnosing diabetes mellitus.

As reviewed by Gerbitz et al., the mitochondrial DNA (mtDNA) has been identified as the gene that is directly related to the pathogenesis of diabetes (Gerbitz, K. D. et al., *Biochim. Biophys. Acta*, 1271, 253–260(1995)). Furthermore, Ames et al. have reported that the aging mechanism involves an increase in the number of impaired mitochondria (Ames, B. N. M. et al., *Proc. Natl. Acad. Sci. U.S.A.*, 90, 7915–7922(1993)), which suggests the possibility that the cause of insulin resistance syndrome may be found in mitochondria since the aging process is accompanied by increased appearance of clinical symptoms of the insulin resistance syndrome.

Hitherto, most pathological studies on mtDNA focused on its biochemical nature, such as mutation or deletion thereof (Shoffner, J. M. and Wallace, D. C., "Oxidative phosphorylation diseases" in *The Metabolic and Molecular Bases of Inherited Disease*, Vol. 1, pp 1535–1610. Scrier C. R., Beaudet A. L., Sly W. S., Valle D., ded., McGraw Hill, International Edition), while only a limited number of studies have dealt with the quantitative aspect of mtDNA. Shin reported that the amount of mtDNA in peripheral blood of a diabetic patient is lower than normal (Shin, C. S., *J. Kor. Diabetes Asso.*, 18, 344–350(1994)), and Antonetti et al. reported that the muscular mtDNA content is low in a diabetic patient (Antonetti, D. A. et al., *J. Clin. Invest.*, 95, 1383–1388(1995)). However, these studies, which measured the mtDNA of diabetes patents by Southern blot analysis having inherently poor reproducibility, have failed to fulfill the need to develop a convenient and reliable method which may be used as an index in diagnosing diabetes prior to the onset of the disease.

SUMMARY OF THE INVENTION

Accordingly, it is a primary object of the present invention to provide a method for predicting the development of type 2 diabetes before the manifestation of the symptoms in a subject.

In accordance with the present invention, there is provided a method for predicting the development of type 2 diabetes in a subject, which comprises measuring the mitochondrial DNA (mtDNA) content in peripheral blood of the subject, comparing the measured mtDNA content with that of a normal control, and predicting the increased risk of development of diabetes when the subject's mtDNA content is lower than that of the normal control.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1A:
FIG. 1A shows that competitive PCR gave 631 bp and 571 bp DNA products derived from mtDNA and competitive PCR, respectively.

The method of the present invention comprises measuring the mitochondrial DNA("mtDNA") content in the peripheral blood sample of a subject for preclinically diagnosing type 2 diabetes. More specifically, the inventive method for predicting type 2 diabetes before the manifestation of its symptoms in a subject comprises: measuring the mitochondrial DNA(mtDNA) content in peripheral blood of the subject, comparing the measured mtDNA content with that of a normal control, and predicting the increased risk of development of diabetes when the subject's mtDNA content is lower than that of the normal control.

The present inventors have discovered that onset of type 2 diabetes is preceded by decreased mitochondrial DNA content in peripheral blood before the manifestation of its symptoms in a subject. Accordingly, quantification of peripheral mtDNA provides a new clinical tool for diagnosing preclinical type 2 diabetes.

The mtDNA content can be measured by employing any conventional methods which utilize Southern blot analysis, competitive PCR method, and slot blot method, wherein the competitive PCR method is more preferred.

Further, the mtDNA content of peripheral blood correlates quantitatively with that of muscle. Therefore, the reduction of the mtDNA content in peripheral blood reflects that in muscle which is the major site of occurrence of insulin resistance in a diabetes patient and, accordingly, determination of mtDNA content in peripheral blood can be a reliable tool for diagnosing type 2 diabetes.

Moreover, the mtDNA content in middle aged people has statistically significant correlations with insulin resistance parameters such as blood pressure and waist-hip ratio (WHR).

The following Reference Examples and Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

Reference Example 1

DNA Extraction from Blood and Quantification

Blood samples taken from test subjects were centrifuged. The buffy coat layer was separated therefrom and stored at −70° C. After the frozen buffy coat layer was thawed, total DNA was extracted therefrom using a QIAmp™ tissue kit(QIAGEN, Chatworth, Calif., U.S.A.) and the total DNA concentration of each sample was measured with a spectrophotometer(Beckman, Fullerton, Calif., U.S.A.).

Reference Example 2

Quantification of mtDNA using Competitive PCR (CPCR)

To quantify the mtDNA content in a small sample, a competitive PCR was conducted as follows.

(Step 1) Preparation of internal standard

Internal standards were used to compare PCR efficiencies and to attenuate the effects caused by inhibitors or the effects brought about by varying amplification efficiencies. The internal standard was designed to use the same primer set as the target gene but to yield a different-sized PCR product; it was prepared by PCR using the primers shown in Table 1. The primers listed in Table 1 were specially designed based on the nucleotide sequence of human mtDNA disclosed in Anderson S. et al.(*Nature*, 290, 457–465(1981)).

TABLE 1

| Primer | 5'-3' Sequence | | Position (Nucleotide No.) |
|---|---|---|---|
| MtF1 | CCTAGGGATAACAGCGCAAT | (SEQ ID NO: 1) | 2928–2947 |
| MtR1 | TAGAAGAGCGATGGTGAGAG | (SEQ ID NO: 2) | 3558–3539 |
| JS3 | GCCATGGGTAGGGCTCTGCCATCTTAACAA | (SEQ ID NO: 3) | 3317–3308, 3247–3228 |
| JS4 | GGCAGAGCCCTACCCATGGCCAACCTCCTA | (SEQ ID NO: 4) | 3238–3247, 3308–3317 |

Two independent PCR amplifications using the sets of mtF1+JS3 and mtR1+JS4 produced DNA fragments having 331 bp and 261 bp, respectively. Each PCR mixture contained 100 ng of genomic DNA, 25 pmole of each primer, 200 $\mu$M of each of dATP, dTTP, dCTP and dGTP, 1 unit of Taq DNA polymerase, 20 mM Tris-Cl(pH 8.3), 1.5 mM MgCl$_2$, 50 mM KCl, 0.05% Tween 20 and 0.001% gelatin. PCR was conducted under the following conditions: one cycle of 3 min. at 94° C., 1 min. at 60° C. and 1 min. at 72° C.; 34 cycles of 40 sec. at 94° C., 1 min. at 60° C. and 1 min. at 72° C.; and final reaction of 10 min. at 72° C. The PCR product was analyzed on the 1.0% agarose gel by electrophoresis.

Secondary PCR amplification using the above products and the primer set of mtF1+mtR1 produced a 571 bp fragment containing the sequences corresponding to 2928$^{th}$–3247$^{th}$ nucleotides and 3308$^{th}$–3558$^{th}$ nucleotides of the mtDNA, with deletion of the intervening 60 bp(position 3248–3307). The composition of the PCR mixture was the same as above except that 1 $\mu$l of each of the 331 bp and 261 bp products were used as a template, and PCR was conducted under the following conditions: 8 cycles of 4 min. at 94° C., 40 sec. at 94° C., 1 min. at 58° C. and 1 min. at 72° C.; 25 cycles of 40 sec. at 94° C., 1 min. at 60° C. and 1 min. at 72° C.; and final reaction of 10 min. at 72° C. The PCR product was analyzed on the 1.0% agarose gel by electrophoresis.

(Step 2) Preparation of a plasmid containing 571 bp fragment

The PCR product of Step 1 was analyzed on the agarose gel by electrophoresis and a band corresponding to the 571 bp fragment was excised therefrom, DNA was extracted from the band by using QIAEX™ II kit(QIAGEN, Chatworth, Calif., U.S.A.). Cloning was conducted by using original TA cloning kit(Invitrogen Therapeutics, Inc., Houston, Tex. 77054, U.S.A.). Specifically, 20 ng of the DNA was added to 50 ng PCR™ II vector and then ligated with T4 DNA ligase.

One shot™ INVaF' competent cell(Invitrogen Therapeutics, Inc., Houston, Tex. 77054, U.S.A.) was transformed with the resulting vector, and the transformants were spread on LB agar plate containing 50 μg/ml of ampicillin and 25 μg/ml of X-gal and then incubated overnight at 37° C. Transformed cells, i.e., white colonies were selected and incubated overnight on LB broth containing 50 μg/ml of ampicillin. The plasmid DNA was extracted therefrom by using QIAGEN plasmid DNA extraction kit(QIAGEN, Chatworth, Calif., U.S.A.).

(Step 3) Competitive PCR

Each of 16.43, 8.21, 4,11, 2.06 and $1.03 \times 10^5$ copies of the plasmid prepared in Step 2 was added as a competitive DNA template to 5 ng of total cellular DNA obtained in Reference Example 1 and subjected to PCR using primers mtF1 and mtR1. The PCR mixture contained 2.5 pmole of each primer, 125 μM of each of dATP, dTTP, dCTP and dGTP, 1 unit of Taq DNA polymerase, 20 mM Tris-Cl(pH 8.3), 1.5 mM $MgCl_2$, 50 mM KCl, 0.05% Tween 20 and 0.001% gelatin.

PCR was conducted under the following conditions: one cycle of 3 min. at 94° C., 40 sec. at 65° C. and 1 min. at 72° C.; 27 cycles of 1 min. at 94° C., 40 sec. at 65° C. and 1 min. at 72° C.; and final reaction of 7 min. at 72° C. The PCR product was analyzed on the 1.0% agarose gel by electrophoresis. Gels were stained with EtBr and photographed under UV light(FIG. 1A), and intensities of the target DNA band(631 bp) and competitor band(571 bp) were measured by using NIH Image software(National Institute of Health, ML, U.S.A.). In FIG. 1, lanes 1 to 5 represent the result of PCR using 16.43, 8.21, 4,11, 2.06 and $1.03 \times 10^5$ copies of standard plasmid, respectively.

Figure 1B:
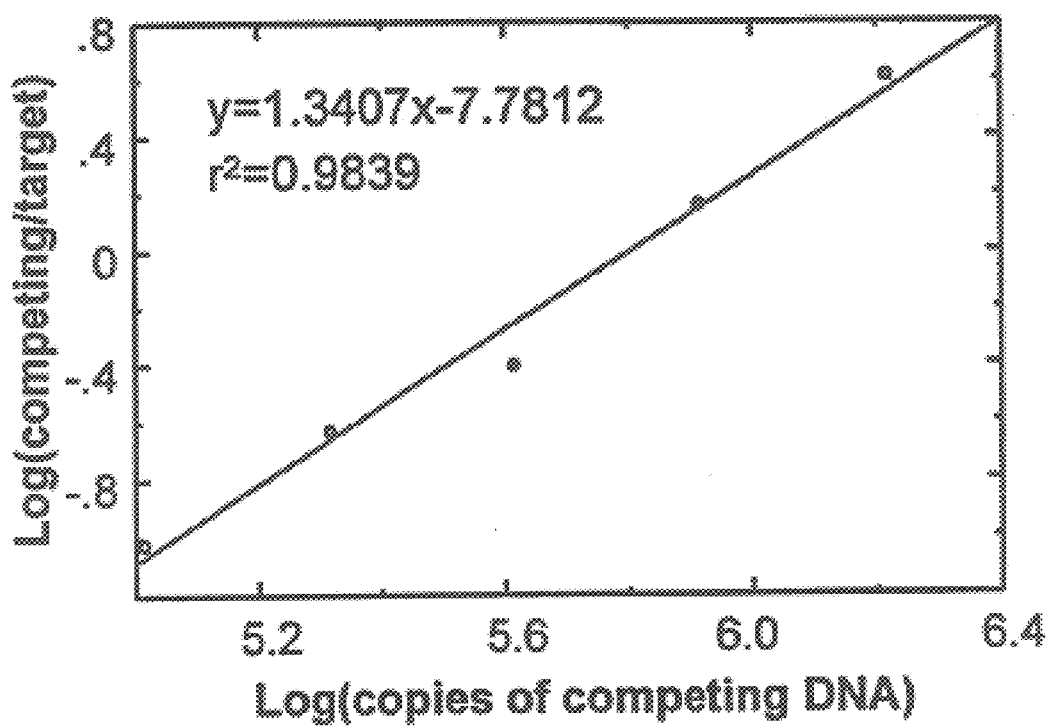
FIG. 1B depicts the determination of competitive equivalence points.
Figure 2A:
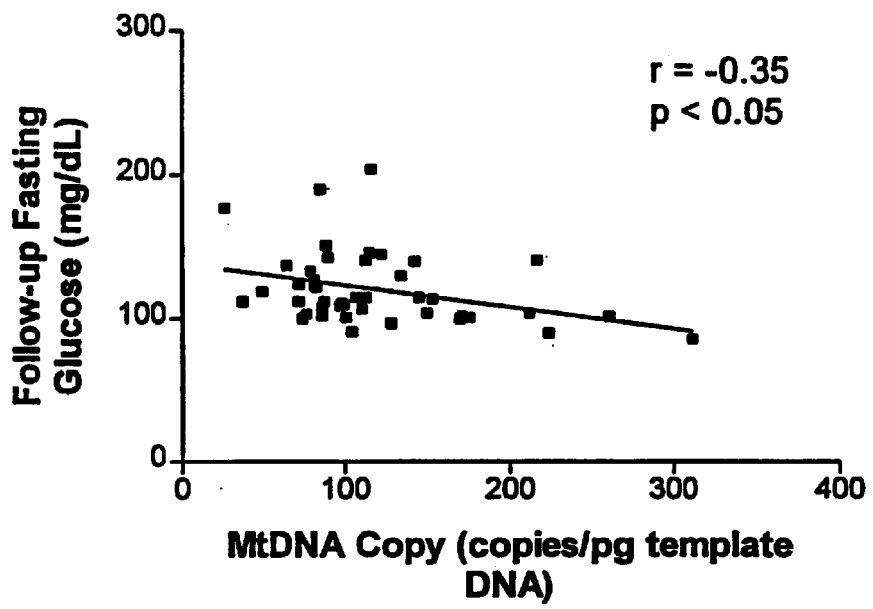
FIG. 2A delineates the correlation of peripheral blood leukocyte mtDNA copy with fasting plasma glucose level at the time of the second survey( 1995)
Figure 2B:
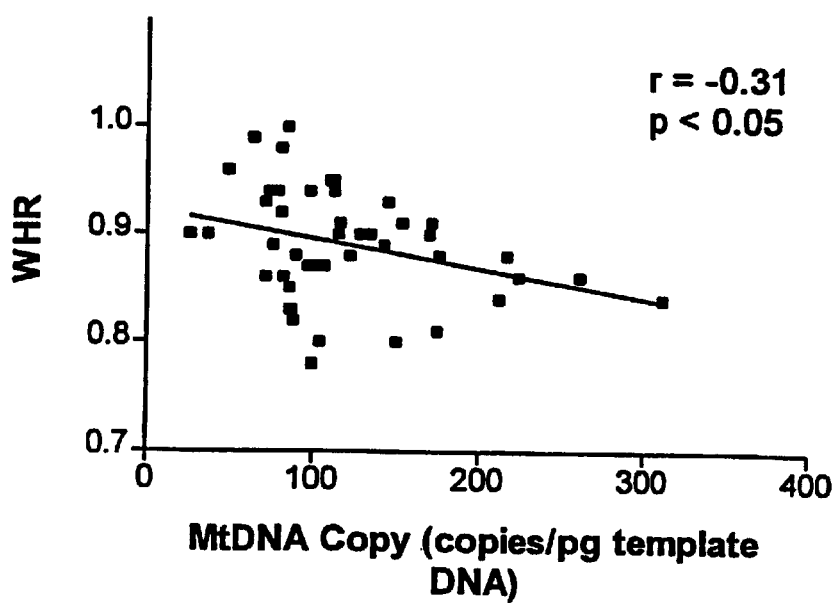
FIG. 2B describes the correlation of peripheral blood leukocyte mtDNA copy with waist-hip ratio at the time of the first survey(1993)
Figure 2C:
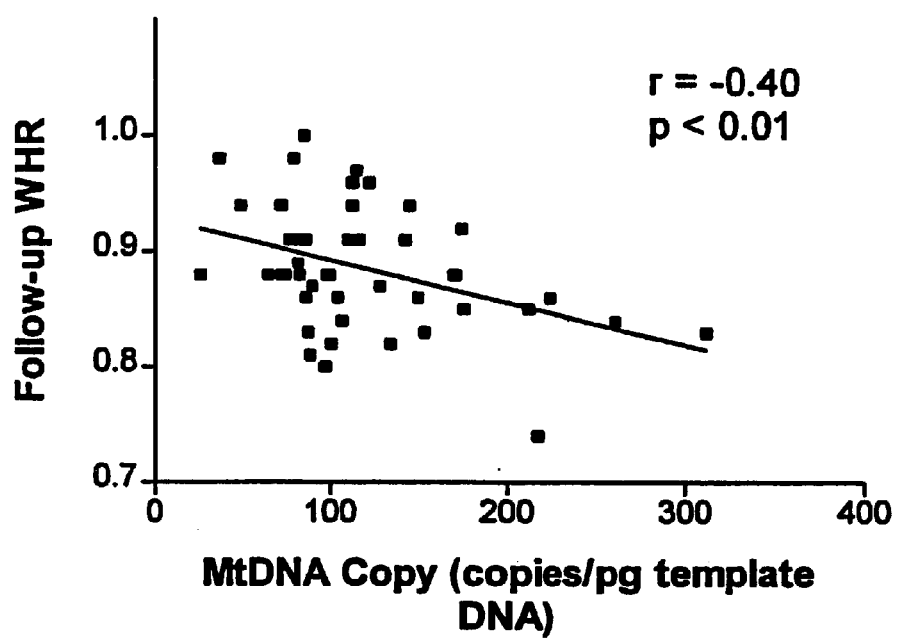
FIG. 2C represents the correlation of peripheral blood leukocyte mtDNA copy with waist-hip ratio at the time of the second survey(1995)
Figure 2D:
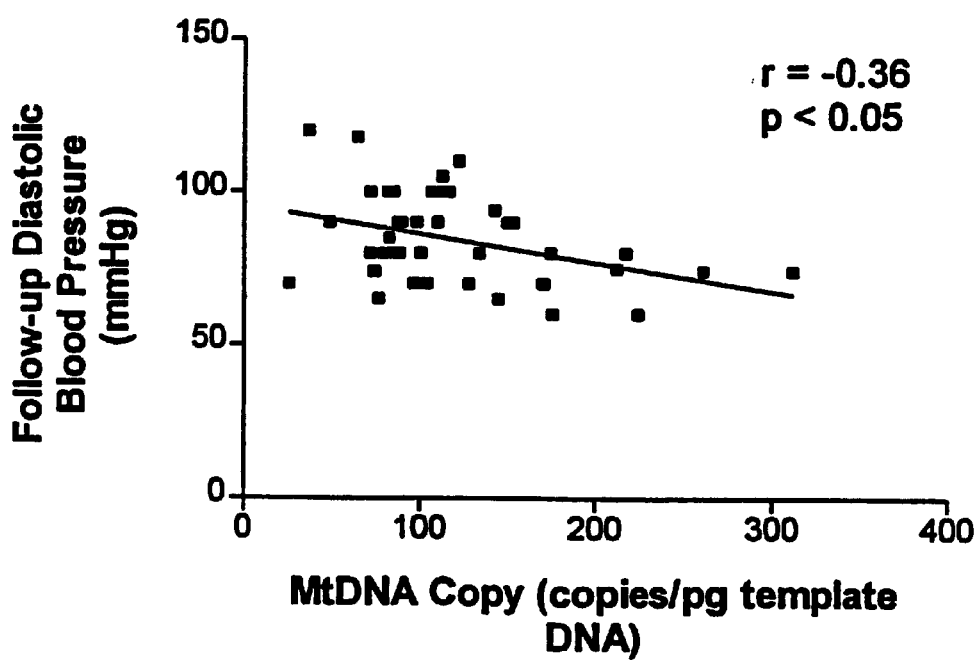
FIG. 2D portrays the correlation of peripheral blood leukocyte mtDNA copy with diastolic blood pressure at the time of the second survey(1995)

The logarithm of the calculated ratio of the signal for the competitive template-derived product to the signal for the mtDNA sequence-derived product was plotted against the logarithm of the copy number of the added competitive template, and competition equivalence points were determined by interpolation. MtDNA content was expressed as copy number per picogram of template DNA. The result is shown in FIG. 1B.

Example 1: mtDNA quantity in subjects who developed diabetes Mellitus

To determine whether decreased mtDNA content in peripheral blood leukocytes precedes the development of diabetes mellitus, stored blood samples from two community-based surveys conducted in Yonchon County, Korea in 1993 and 1995 were utilized. 23 newly diagnosed diabetic patients and 22 age- and sex-matched controls were selected from 1197 subjects who participated in both the first(1993) and the second(1995) survey.

Diagnosis of diabetes mellitus was conducted based on World Health Organization criteria(WHO Technical Report Series, No. 646, 8–12(1980)). Patients with newly developed diabetes were those who had not been diabetic at the time of the first survey in 1993 but became diabetic by the time of the second survey conducted two years later. Control subjects were those who were still non-diabetic at the time of the second survey. Peripheral blood samples collected during the first survey in 1993 were retrieved for mtDNA quantification.

The mtDNA content of each of the samples were measured in accordance with the procedures of Reference Examples 1 and 2. The characteristics and mtDNA quantity of subjects who developed diabetes mellitus within two years are shown in Table 2, wherein p value denotes the statistical power on the significance of difference in the listed variables between the converters and non-converters.

TABLE 2

Clinical characteristics of the subjects

| | Converters to diabetes (n = 23) | Non-converters (n = 22) | p-value |
|---|---|---|---|
| Age | 61.0 ± 13.0 | 58.0 ± 14.0 | NS* |
| Sex (M/F) | 13/10 | 14/8 | NS |
| MtDNA (copies/pg Template DNA) | 102.8 ± 41.5 | 137.8 ± 67.7 | <0.05 |
| Body mass index (BMI) ($kg/m^2$) | 24.7 ± 4.2 | 23.4 ± 2.6 | NS |
| Waist-hip ratio (WHR) | 0.90 ± 0.05 | 0.88 ± 0.05 | NS |
| Fasting glucose (mg/dl) | 106.4 ± 14.0 | 100.3 ± 9.7 | NS |
| Post-load glucose (mg/dl) | 117.0 ± 28.0 | 120.5 ± 31.7 | NS |
| Systolic blood pressure (mmHg) | 133.0 ± 18.0 | 127.0 ± 21.0 | NS |
| Diastolic blood pressure (mmHg) | 83.0 ± 12.0 | 83.0 ± 16.0 | NS |
| Fasting insulin (uIU/ml) | 7.3 ± 1.4 | 7.4 ± 1.8 | NS |
| Proinsulin (pmol/L) | 13.3 ± 7.8 | 8.4 ± 5.2 | NS |
| Cholesterol (mg/dl) | 162.1 ± 37.0 | 155.8 ± 29.3 | NS |
| Triglyceride (mg/dl) | 144.7 ± 69.4 | 121.6 ± 79.0 | NS |
| HDL-cholesterol (mg/dl) | 36.9 ± 8.9 | 33.0 ± 9.0 | NS |

*NS: Not significant

As shown in Table 2, there were no significant differences in initial anthropometric parameters, blood pressure and lipid profiles between subjects who became diabetic and those who did not. However, the mean mtDNA value for the converters was 102.8±41.5 copies/pg template DNA which is significantly lower than 137.8±67.7 copies/pg template DNA found for controls($p<0.05$).

Example 2: Correlation between mtDNA quantity and various parameters

Various parameters of insulin resistance syndrome such as waist-hip ratio(WHR), fasting glucose level and diastolic blood pressure were measured by conventional methods and then plotted against individual mtDNA content of all subjects including both converters and non-converters. Correlations between mtDNA content and the parameters were analyzed by Pearson's correlation.

The results are shown in FIGS. 2A to 2D and Table 3, wherein significant inverse correlations were noted between mtDNA content and WHR($r=-0.31$, $p<0.05$) measured in the first survey(1993), and fasting glucose level($r=-0.35$, $p<0.05$), diastolic blood pressure($r=-0.36$, $p<0.05$) and WHR(($r=-0.40$, $p<0.01$) measured in the second survey. Correlations with serum levels of total and high-density cholesterol, triglyceride, insulin and proinsulin were not statistically significant.

TABLE 3

Correlation between mtDNA content and various parameters

| Index | n | r value | p value |
|---|---|---|---|
| Age | | −0.08 | 0.587 |
| Systolic Blood Pressure | 93 | −0.26 | 0.087 |
| (SBP) | 95 | −0.28 | 0.067 |
| Diastolic Blood Pressure | 93 | −0.21 | 0.170 |
| (DBP) | 95 | −0.36 | 0.015 |
| Waist-Hip Ratio | 93 | −0.31 | 0.036 |
| (WHR) | 95 | −0.40 | 0.007 |
| Fasting Blood Sugar | 93 | −0.15 | 0.324 |
| (FBS) | 95 | −0.35 | 0.019 |
| 2 hr Blood Glucose Level after | 93 | −0.11 | 0.469 |
| 75 g Oral Glucose Load (Glu2) | 95 | −0.35 | 0.092 |
| Body Mass Index (BMI) | 93 | −0.21 | 0.169 |
| | 95 | −0/24 | 0.117 |

Example 3: Correlation between Insulin Sensitivity Index and Peripheral Blood mtDNA Content (1) Subjects Eighty-two subjects who had parents having type 2 diabetes were recruited in from the Mokdong cohort study established in Seoul, Korea in 1997, which was consisted of 750 healthy adults above 30 years old. Subjects having the past history of diabetes mellitus, hypertension and atherosclerotic heart disease were excluded in this study.

All subjects underwent a 75-g oral glucose tolerance test. They were classified into 3 groups: with normal glucose tolerance (NGT), with impaired glucose tolerance (IGT) and with newly diagnosed diabetes (DM) according to the WHO criteria. For the control group, age-, sex- and body mass index-matched subjects without a family history of diabetes were randomly selected from the cohort.

(2) Measurement of anthropometric parameters

The blood pressure, height, weight, and circumferences of waist and hip of the subjects were measured by conventional methods. Total body fat content, expressed as fat mass (kg) was determined using bioelectric impedance analyzer (Inbody 2.0, Biospace CO., Ltd.). Percent body fat (%) was calculated using the following formula: fat mass (kg) divided by body weight (kg)×100. Subcutaneous and visceral fat areas were measured and calculated using the computerized tomography conducted at the umbilical level.

(3) Measurements of biochemical parameters

Plasma glucose concentrations were measured by glucose oxidase method (YSI glucose analyzer, Yellow Springs Instrument, Yellow Springs, Ohio, USA). Plasma total cholesterol, triglyceride and HDL-cholesterol were determined by enzymatic methods using Hitachi 7150 autochemistry analyzer. Nonesterified fatty acid (NEFA) was measured by enzymatic method (NEFAzyme kit, Eiken, Japan). Serum insulin (Diagnostic Products Co, USA), C-peptide (Diagnostic Product Co., USA) and leptin (Linco, USA) were measured by radioimmunoassay.

(4) Measurements of insulin sensitivity

Insulin sensitivity was determined using Insulin-modified frequently sampled intravenous glucose tolerance test of Bergman(Bergman, R. N. et al., *Am. J. Physiol.*, 236: E667–77, 1979).

In brief, fasting blood samples were taken for measurement of plasma glucose and insulin levels following a 14 hour overnight fasting. Glucose (0.3 g/kg of body weight) as a form of 20% glucose solution was intravenously injected over 60 seconds via 18 gauge-cannula in the arm other than the sampling arm. Additional blood samples were taken at 2, 3, 4, 5, 6, 8, 19, 22, 30, 40, 50, 70, 100 and 180 minutes following injection of glucose. At 20 min. post glucose injection, regular insulin (0.0125 U/kg body weight) was administered intravenously to increase the accuracy of the modeling analyses. Insulin sensitivity index (SI) and insulin dependent glucose elimination (glucose effectiveness; SG) were calculated using MINMOD 2.0 software.

(5) Quantification of mitochondrial DNA

Total DNA was extracted from peripheral blood leukocytes in accordance with Reference Example 1. The mtDNA content was determined using real-time quantitative PCR method (ABI Prism 7700) and a mitochondria-specific fluorescent probe. The internal probe labeled with two fluorescent dyes, 5-carboxyfluorescein (FAM) on the 5' end and N,N,N,N-tetramethyl 6-carboxyrhodamine (TAMRA) on the 3' end, was prepared by a DNA synthesizer (Perkin Elmer).

The sequences of the probe and PCR primers are described below:

mtDNA amplicon 265 bp
forward primer: 5'-ACGACCTCGATGTTGGATC-3' (position 2981–3000; SEQ ID NO.: 5)
reverse primer: 5'-GCTCTGCCATCTTAACAAACC-3' (position 3245–3224; SEQ ID NO.: 6)
probe: 5'-TTCAGACCGGAGTAATCCAGGTCG-3' (position 3071–3095; SEQ ID NO.: 7)

The probes hybridized within the 265 bp region were amplified with PCR primers. When the two dyes are in close proximity, with an intact oligonucleotide probe, TAMRA acts as a quencher for FAM by absorbing at the FAM emission region. The 5' exonuclease activity of Taq degrades the hybridizing probe during PCR. Degradation of the probe leads to separation of two dyes with an increase in the intensity of fluorescence. The amount of fluorescence measured in a sample is proportional to the amount of specific PCR product generated. The amount of product in a particular reaction mixture is measured by interpolation using a standard Ct curve generated from known starting DNA concentrations.

The MtDNA content was corrected by 28s ribosomal RNA (rRNA) content, which was simultaneously measured using real-time PCR method. The primers for 28s rRNA were forward primer, 5'-TTAAGGTAGCCAAATGCCTCG-3'(7358–7378; SEQ ID NO: 8) and reverse primer, 5'-CCTTGGCTGTGGTTTCGCT-3'(7460–7441, SEQ ID NO: 9) and the probe was 5'- TGAACGAGATTCCCACTGTCCCTACCTA CTATC-3'(SEQ ID NO: 10).

The PCR mixture consisted of primers(each 10 pmoles), 200 nM Taqman probe, dATP, dCTP and dGTP, each at a concentration of 200 nM, 400 nM dUTP, 4.5 mM $MgCl_2$, 1.25 U AmpliTaq DNA polymerase, 0.5 U AmpErase Uracil N-glycosylase(UNG), and 1x PCR buffer A. Amplification and detection were performed with the ABI Prism 7700 system under the following condition: 1 cycle of 50° C. for 2 min, 1 cycle of 95° C. for 10 min, and 40 cycles of 95° C. for 15 sec and 60° C. for 1 min. The mtDNA content was expressed as mtDNA content/28s rRNA content.

(6) Statistical analysis

All data was presented as mean ± standard error mean (SEM). Difference between diabetic offspring and control was compared by student's t-test. Correlation of mtDNA content with indexes for insulin sensitivity and other parameters of the insulin resistance syndrome was determined using Pearson's correlation and the multiple linear regression analysis. Values at $P<0.05$ were considered to be significant.

Figure 3:
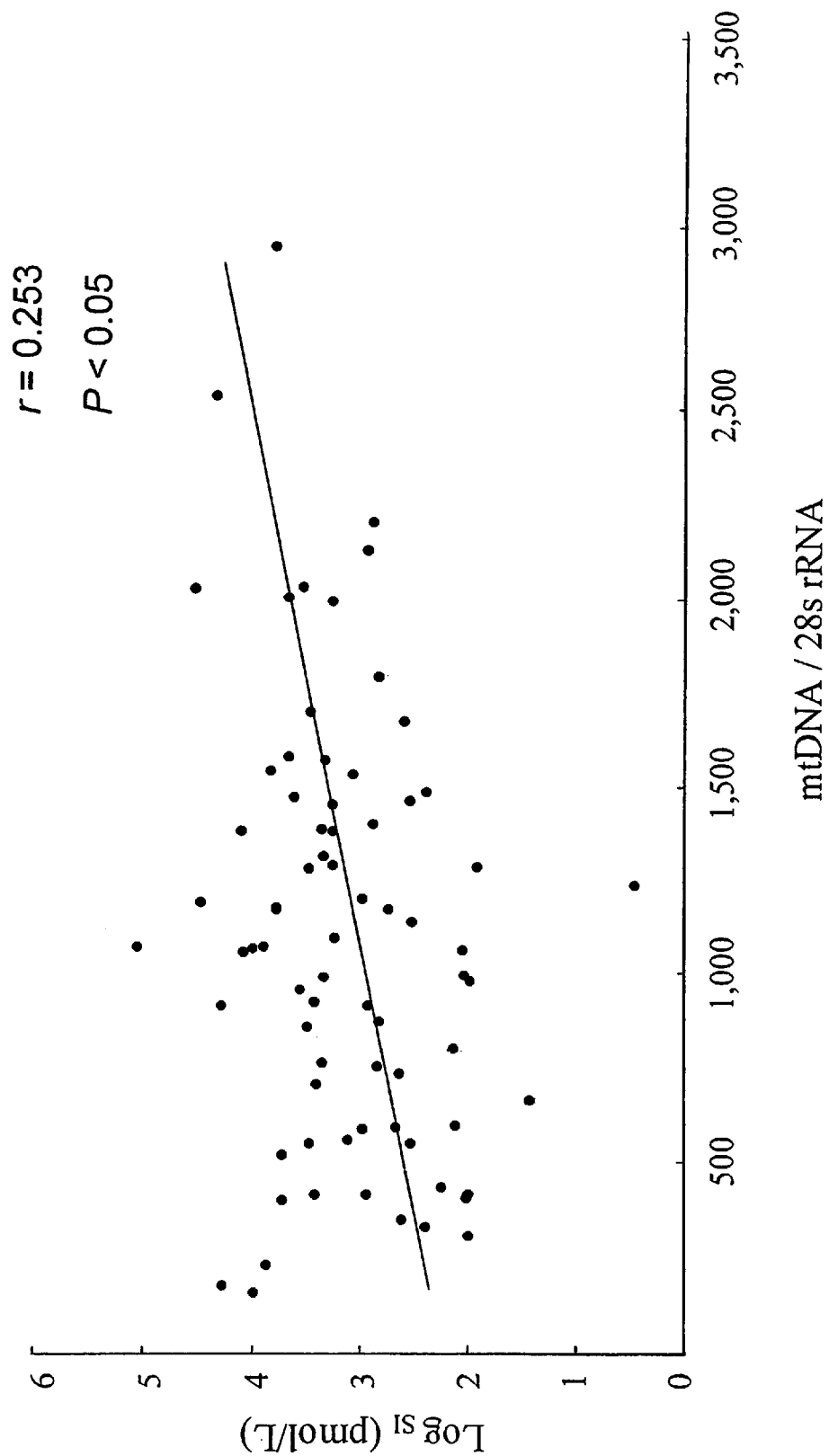
FIG. 3 presents the correlation between insulin sensitivity index and peripheral blood mtDNA content.

The results are shown in Tables 4 to 7 and FIG. 3.

TABLE 4

Clinical characteristics of the subjects

| | | Offspring | | |
|---|---|---|---|---|
| Variable | Control (n = 52) | NGT (n = 52) | IGT (n = 21) | New DM (n = 9) |
| Age (yr) | 41.8 ± 0.9 | 41.7 ± 0.9 | 45.1 ± 1.3 | 50.6 ± 1.9* |
| Sex (M/F) | 17/35 | 18/34 | 11/10 | 4/5 |
| Body mass index (kg/m$^2$) | 24.0 ± 0.3 | 23.7 ± 0.4 | 24.2 ± 0.7 | 25.8 ± 0.7* |
| Waist to hip ratio | 0.82 ± 0.0 | 0.82 ± 0.0 | 0.84 ± 0.0 | 0.87 ± 0.0* |
| Fasting glucose (mmol/l) | 4.8 ± 0.1 | 5.0 ± 0.1 | 5.3 ± 0.2† | 7.7 ± 0.8* |
| Fasting insulin (pmol/l) | 60.0 ± 5.2 | 46.9 ± 2.8 | 60.0 ± 9.7 | 87.3 ± 16.8* |
| Fasting C-peptide (ng/ml) | 1.4 ± 0.1 | 0.6 ± 0.1 | 0.6 ± 0.1 | 0.8 ± 0.0 |
| Systolic BP (mmHg) | 117.2 ± 1.9 | 116.9 ± 1.8 | 121.0 ± 2.8 | 121.1 ± 3.5 |
| Diastolic BP (mmHg) | 76.5 ± 1.3 | 75.7 ± 1.3 | 80.0 ± 2.3 | 76.7 ± 3.7 |
| Cholesterol (mmol/l) | 4.8 ± 0.1 | 4.9 ± 0.1 | 5.5 ± 0.2 | 5.8 ± 0.4* |
| Triglyceride (mmol/l) | 1.4 ± 0.1 | 1.6 ± 0.2 | 2.4 ± 0.5 | 1.8 ± 0.2 |
| HDL (mmol/l) | 1.2 ± 0.0 | 1.2 ± 0.0 | 1.2 ± 0.1 | 1.2 ± 0.1 |
| Fatty acid (g/l) | 0.3 ± 0.0 | 0.3 ± 0.0 | 0.4 ± 0.1 | 0.3 ± 0.1 |

1. Values are mean ± SEM.
2. NGT, normal glucose tolerance; IGT, impaired glucose tolerance; DM, diabetes mellitus; BP, blood pressure; HDL, high density lipoprotein.
3. *$P < 0.05$ vs control, NGT and IGT. †$P < 0.05$ vs control and NGT.

TABLE 5

Patterns of body fat distribution and indices of insulin secretion and resistance of the subjects

| | | Offspring | | |
|---|---|---|---|---|
| Variable | Control (n = 52) | NGT (n = 52) | IGT (n = 21) | New DM (n = 9) |
| Fat mass (kg) | 17.6 ± 1.3 | 16.9 ± 0.6 | 16.9 ± 1.1 | 18.3 ± 1.2 |
| Percent body fat (%) | 27.9 ± 1.3 | 26.7 ± 0.6 | 25.5 ± 1.2 | 26.6 ± 1.2 |
| Visceral fat area (cm$^2$) | 61.9 ± 8.5 | 75.0 ± 4.7 | 87.8 ± 9.1 | 132.8 ± 13.5* |
| VSR | 0.40 ± 0.1 | 0.49 ± 0.0 | 0.57 ± 0.1 | 0.73 ± 0.0* |
| Leptin (ng/ml) | 5.8 ± 1.2 | 7.1 ± 1.1 | 8.2 ± 2.0 | 7.1 ± 0.8 |
| SI (10$^{-4}$/pmol/l) | 0.98 ± 0.1 | 0.84 ± 0.1 | 0.83 ± 0.2 | 0.34 ± 0.1* |
| SG (10$^{-2}$/min) | 2.29 ± 0.0 | 2.18 ± 0.0 | 1.94 ± 0.0 | 2.52 ± 0.1 |
| AIR (pmol/l) | 318.9 ± 46.1 | 231.2 ± 29.8‡ | 157.8 ± 34.9† | 29.2 ± 15.6* |

1. Values are mean ± SEM.
2. NGT, normal glucose tolerance; IGT, impaired glucose tolerance; DM, diabetes mellitus; VSR, visceral to subcutaneous ratio; SI, insulin sensitivity index; SG, glucose effectiveness; AIR, acute insulin response.
3. *$P < 0.05$ vs control, NGT and IGT. †$P < 0.05$ vs control and NGT. ‡$P < 0.05$ vs control.

TABLE 6

Pearson's correlation coefficiencies between peripheral blood mtDNA content and various clinical parameters in total subjects

| Variable | r | P-value |
|---|---|---|
| Age | −0.142 | NS |
| Body mass index | −0.059 | NS |
| Waist to hip ratio | −0.006 | NS |
| Systolic blood pressure | 0.03 | NS |
| Diastolic blood pressure | −0.049 | NS |
| Fasting glucose | −0.035 | NS |
| Fasting insulin | −0.053 | NS |
| Fasting C-peptide | −0.248 | 0.032 |
| Visceral fat area | −0.198 | 0.057 |
| Visceral to subcutaneous ratio | −0.131 | NS |
| Leptin | −0.013 | NS |
| SI | 0.214 | 0.033 |
| SG | 0.07 | NS |
| Acute insulin response | −0.059 | NS |

1. NS, not significant
2. SI, insulin sensitivity index; SG, glucose effectiveness.

TABLE 7

Multiple linear regression analysis for peripheral blood mtDNA content affecting the insulin sensitivity in offspring of patients with type 2 diabetes mellitus

| Independent Variables | β | R$^2$ | F | P-value |
|---|---|---|---|---|
| mtDNA content | 0.0014 | 0.046 | 4.65 | 0.033 |
| age, mtDNA content | 0.0014 | 0.05 | 2.426 | 0.040 |
| age, BMI, mtDNA content | 0.0012 | 0.14 | 4.909 | 0.074 |
| age, BMI, fasting insulin, mtDNA content | 0.0007 | 0.236 | 6.70 | 0.246 |

1. BMI, body mass index.
2. Insulin sensitivity index using logarithmic transformation was used as a dependent variable.

FIG. 3 presents the correlation between insulin sensitivity index and peripheral blood mtDNA content.

Example 4: Correlation between mtDNA Contents in Peripheral Blood with That in Muscle (Step 1) DNA Extraction from Blood and Muscle and Quantification of the Extracted DNA Blood samples were taken from thirty-six 9 to 10 week-old Sprague-Dawley rats each weighing about 200 to 250 g, and centrifuged. The buffy coat layer was separated therefrom and stored at −70° C. After the frozen buffy coat layer was thawed, total DNA was extracted and its concentration was measured in accordance with the method of Reference Example 1.

On the other hand, about 100 mg of the femoral muscle was separated from each of the rats and stored at −70° C. After the frozen muscle was thawed, it was homogenized in 1 ml of a lysis buffer(10 mM Tris, 100 mM NaCl, 25 mM EDTA, 1% SDS, 100 μg/ml proteinase-K) and incubated in a 48° C. water-bath for 14 to 16 hours. After further incubation at 37° C. for 30 min., total DNA was extracted therefrom with phenol/chloroform in accordance with a conventional method(Sambrook, et al., *Molecular cloning; A Laboratory Manual.* $2^{nd}$ ed,. Cold Spring Harbor Laboratory Press, N.Y., 1989). 100 μl, of 10 mM Tris-1 mM EDTA was added to the extracted DNA and the total DNA concentration of each sample was measured at 260 nm with a spectrophotometer(Beckman, Fullerton, Calif., U.S.A.).

(Step 2) Quantification of mtDNA using Competitive PCR (CPCR)

To quantify the mtDNA content in the blood and the muscle samples prepared as above, a competitive PCR was conducted as follows.

(1) Preparation of internal standard and a plasmid containing 694 bp fragment

Internal standards were prepared by PCR using the primers shown in Table 8, in accordance with the method of (Step 1) of Reference Example 2. The primers listed in Table 8 were specially designed based on the nucleotide sequence of rat mtDNA disclosed in Anderson S. et al.(*Nature*, 290, 457–465(1981)).

Further, plasmid containing the PCR product was prepared in accordance with the method of (Step 2) of Reference Example 2.

(2) Competitive PCR

The molecular weight of the plasmid DNA obtained in (1) was $3.00 \times 10^6$ mole and, accordingly, 1 ng of the plasmid DNA corresponded to 333 amoles.

Each of 133.20, 66.60, 33.30, 16.65 and 8.33 amoles of the plasmid DNA prepared in (1) was added as a competitive DNA template to 50 ng of total cellular DNA(target DNA) obtained from blood or muscle in (Step 1) and subjected to PCR using primers MT3 and MT4. The PCR mixture contained 50 pmol of each primer, 200 mM of each of DATP, dTTP, dCTP and dGTP, 0.75 unit of Taq DNA polymerase, 20 mM Tris-Cl(pH 8.3), 1.5 mM $MgCl_2$, 50 mM KCl, 0.05% Tween 20 and 0.001% gelatin.

PCR was conducted under the following conditions: one cycle of 3 min. at 94° C., 1 min. at 60° C. and 1 min. at 72° C.; 30 cycles of 40 sec. at 94° C., 1 min. at 60° C. and 1 min. at 72° C.; and final elongation reaction of 7 min. at 72° C.

The PCR product was analyzed on 1.5% agarose gel by electrophoresis. Gels were stained with EtBr and photographed under UV light, and intensities of the target DNA band(770 bp) and competitor band(694 bp), i.e., internal standard, were measured by using NIH Image software (National Institute of Health, ML, U.S.A). Since various concentrations of internal standard DNA were employed, the concentration of target DNA was determined from that of internal standard DNA when the intensity of its band is equal to that of the internal standard DNA.

Figure 4:
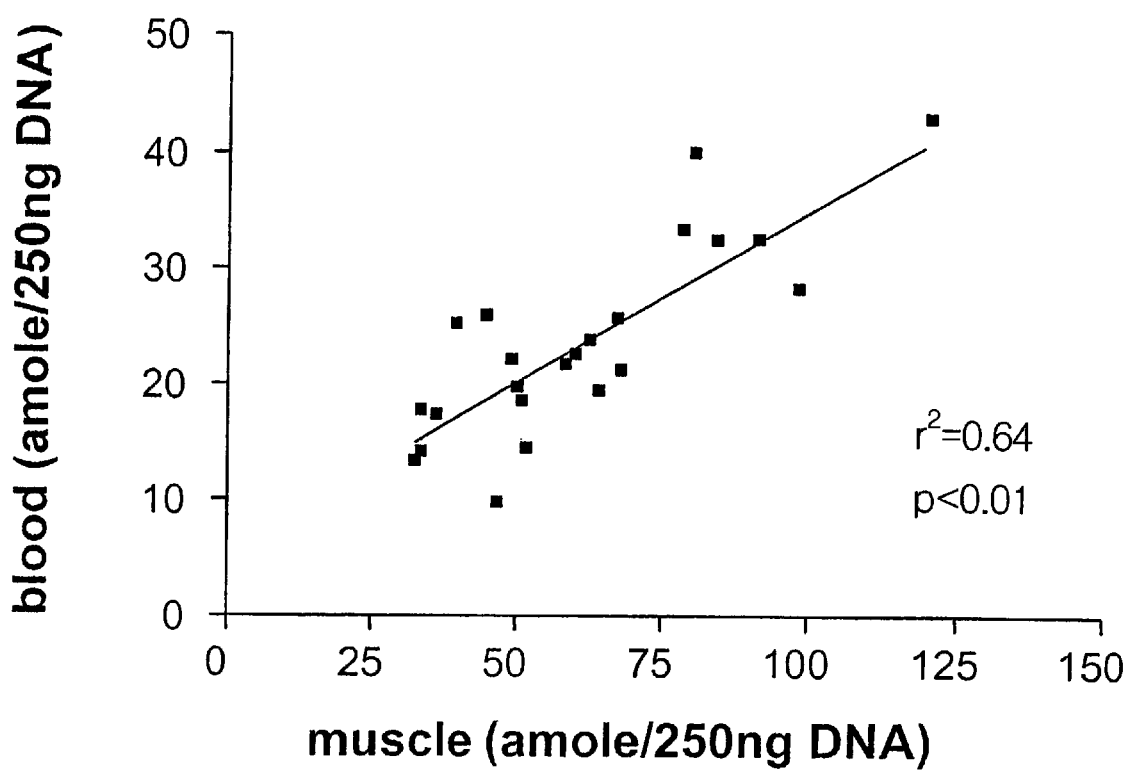
FIG. 4 discloses the correlation between the amount of peripheral blood leukocyte mtDNA and that of mtDNA in muscle.

As shown in FIG. 4, the mtDNA content of peripheral blood correlates quantitatively with that of muscle. Therefore, it is concluded that the reduction of the mtDNA

TABLE 8

| Primer | 5'-3' Sequence | | | | Position (Nucleotide No.) |
|---|---|---|---|---|---|
| MT3 | AGGACTTAACCAGACCCAAACACG | (SEQ | ID | NO: 11) | 4395–4418 |
| MT4 | CCTCTTTTCTGATAGGCGGG | (SEQ | ID | NO: 12) | 5164–5145 |
| Df1 | CCCTATCAACCCAACCAACAACAACTCCAA | (SEQ | ID | NO: 13) | 4721–4730, 4807–4826 |
| Dr1 | TGTTGGTTGGGTTGATAGGGTTGAGCAGTT | (SEQ | ID | NO: 14) | 4816–4807, 4730–4711 |

Two independent PCR amplifications using the sets of MT3+Dr1 and MT4+Df1 produced DNA fragments having 346 bp and 369 bp, respectively.

Secondary PCR amplification using the above products and the primer set of MT3+MT4 produced a 694 bp fragment containing the sequences corresponding to $4395^{th}$–$4730^{th}$ nucleotides and $4807^{th}$–$5164^{th}$ nucleotides of the mtDNA, with deletion of the intervening 76 bp(position 4731–4806).

content in peripheral blood reflects that in muscle which is the major site of insulin resistance in diabetes and, accordingly, determination of mtDNA content in peripheral blood can be a reliable tool for diagnosing of diabetes.

While the invention has been described with respect to the above specific embodiments, it should be recognized that various modifications and changes may be made to the invention by those skilled in the art which also fall within the scope of the invention as defined by the appended claims.

What is claimed is:

1. A method for predicting the development of type 2 diabetes before the manifestation of its symptoms in a subject, which comprises measuring the mitochondrial DNA (mtDNA) content in peripheral blood of the subject, comparing the measured mtDNA content with that of a normal control, and predicting the increased risk of development of diabetes when the subject's mtDNA content is lower than that of the normal control.

2. The method of claim 1, wherein the mitochondrial DNA content in peripheral blood is measured using the competitive polymerase chain reaction(CPCR) method.

* * * * *

UNITED STATES PATENT AND TRADEMARK OFFICE
CERTIFICATE OF CORRECTION

PATENT NO. : 6,232,078 B1
DATED : May 15, 2001
INVENTOR(S) : Hong-Kyu Lee et al.

It is certified that error appears in the above-identified patent and that said Letters Patent is hereby corrected as shown below:

<u>Title page,</u>
Insert the following: -- Foreign Application Priority Data
-Feb. 21, 1997 (KR) 97-5382 --

Signed and Sealed this

Second Day of April, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 6,232,078 B1
DATED : May 15, 2001
INVENTOR(S) : Hong-Kyu Lee et al.

It is certified that error appears in the above-identified patent and that said Letters Patent is hereby corrected as shown below:

<u>Title page,</u>
Item [73], the name of the assignee should read:
-- Mitocon Ltd., Seoul (KR) --

Signed and Sealed this

Thirteenth Day of May, 2003

JAMES E. ROGAN
*Director of the United States Patent and Trademark Office*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 1:

CCTAGGGATA ACAGCGCAAT                                      20

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 2:

TAGAAGAGCG ATGGTGAGAG                                      20

(2) INFORMATION FOR SEQ ID NO: 3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 3:

GCCATGGGTA GGGCTCTGCC ATCTTAACAA                           30

(2) INFORMATION FOR SEQ ID NO: 4:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 4:

GGCAGAGCCC TACCCATGGC CAACCTCCTA                           30

(2) INFORMATION FOR SEQ ID NO: 5:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: oligonucleotide DNA (xi) SEQUENCE DESCRIPTION: SEQ ID NO: 5:

```
ACGACCTCGA TGTTGGATC                                                    19

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 6:

GCTCTGCCAT CTTAACAAAC C                                                 21

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 7:

TTCAGACCGG AGTAATCCAG GTCG                                              24

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 8:

TTAAGGTAGC CAAATGCCTC G                                                 21

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 9:

CCTTGGCTGT GGTTTCGCT                                                    19

(2) INFORMATION FOR SEQ ID NO: 10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 10:

TGAACGAGAT TCCCACTGTC CCTACCTACT ATC                                    33
```

-continued (2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 11:

AGGACTTAAC CAGACCCAAA CACG    24

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 12:

CCTCTTTTCT GATAGGCGGG    20

(2) INFORMATION FOR SEQ ID NO: 13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 13:

CCCTATCAAC CCAACCAACA ACAACTCCAA    30

(2) INFORMATION FOR SEQ ID NO: 14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: oligonucleotide DNA (xi) SEQUENCE DESCRIPTION: SEQ ID NO: 14:

TGTTGGTTGG GTTGATAGGG TTGAGCAGTT    30